(12) United States Patent
Notz et al.

(10) Patent No.: US 10,441,344 B2
(45) Date of Patent: Oct. 15, 2019

(54) SURGICAL APPARATUS COMPRISING A NERVE TESTING DEVICE

(75) Inventors: Juergen Notz, Dettingen (DE); Juergen Beller, Gomaringen (DE)

(73) Assignee: ERBE ELEKTROMEDIZIN GMBH, Tuebingen (DE)

( * ) Notice: Subject to any disclaimer, the term of this patent is extended or adjusted under 35 U.S.C. 154(b) by 1964 days.

(21) Appl. No.: 12/936,948

(22) PCT Filed: Apr. 7, 2009

(86) PCT No.: PCT/EP2009/002571
§ 371 (c)(1),
(2), (4) Date: Oct. 8, 2010

(87) PCT Pub. No.: WO2009/124726
PCT Pub. Date: Oct. 15, 2009

(65) Prior Publication Data
US 2011/0034826 A1 Feb. 10, 2011

(30) Foreign Application Priority Data
Apr. 10, 2008 (DE) .................. 10 2008 018 262

(51) Int. Cl.
| A61B 18/10 | (2006.01) |
| A61B 18/12 | (2006.01) |
| A61B 5/04 | (2006.01) |
| A61B 5/00 | (2006.01) |
| A61B 18/00 | (2006.01) |
| A61N 1/36 | (2006.01) |

(52) U.S. Cl.
CPC ...... *A61B 18/1206* (2013.01); *A61B 5/04001* (2013.01); *A61B 5/4893* (2013.01); *A61B 2018/00434* (2013.01); *A61B 2018/00732* (2013.01); *A61B 2018/00916* (2013.01); *A61B 2018/1266* (2013.01); *A61N 1/36014* (2013.01)

(58) Field of Classification Search
CPC .. A61B 2018/00434; A61B 2018/0044; A61B 2018/00446; A61B 2018/0072; A61B 2018/00767
USPC .................. 606/34, 38; 607/48, 114–118
See application file for complete search history.

(56) References Cited

U.S. PATENT DOCUMENTS

| 5,591,217 A | * | 1/1997 | Barreras | ............ A61N 1/37223 |
| | | | | 607/61 |
| 5,836,943 A | * | 11/1998 | Miller, III | ........................ 606/34 |
| 6,139,545 A | * | 10/2000 | Utley et al. | ...................... 606/34 |

(Continued)

FOREIGN PATENT DOCUMENTS

| JP | 2001-507248 A | | 6/2001 | |
| WO | WO9102559 | * | 3/1991 | ............... A61N 1/32 |

(Continued)

OTHER PUBLICATIONS

Seifart, M., "Analoge Schaltungen", VEB-Verlag Technik Berlin, 1988, p. 386, ISBN 3-341-00624-9.

*Primary Examiner* — Jaymi E Della
(74) *Attorney, Agent, or Firm* — Blank Rome LLP

(57) ABSTRACT

A surgical apparatus for facilitating testing nerves during HF surgery. The surgical apparatus comprises a converter for converting a high-frequency treatment current into a nerve stimulating current. A controllable selector switch optionally feeds either the treatment current or the nerve stimulating current to the electrosurgical instrument.

7 Claims, 2 Drawing Sheets

(56) References Cited

U.S. PATENT DOCUMENTS

| | | |
|---|---|---|
| 6,618,626 B2 | 9/2003 | West, Jr. et al. |
| 6,706,016 B2 * | 3/2004 | Cory et al. .................... 604/117 |
| 6,819,957 B1 * | 11/2004 | Le .................................. 607/62 |
| 2002/0095199 A1 | 7/2002 | West, Jr. et al. |
| 2004/0172083 A1 * | 9/2004 | Penner ............................ 607/35 |
| 2005/0283148 A1 | 12/2005 | Janssen et al. |
| 2006/0167447 A1 * | 7/2006 | Pozzato ......................... 606/37 |
| 2006/0184164 A1 | 8/2006 | Malis et al. |

FOREIGN PATENT DOCUMENTS

| | | |
|---|---|---|
| WO | WO 97/23169 A1 | 7/1997 |
| WO | WO 00/13599 A1 | 3/2000 |
| WO | WO 00/13600 A1 | 3/2000 |
| WO | WO 01/12089 A1 | 2/2001 |

* cited by examiner

SURGICAL APPARATUS COMPRISING A NERVE TESTING DEVICE

BACKGROUND

The invention relates to a surgical apparatus for testing nerves.

In high-frequency surgery ("HF surgery"), tissue structures are cut or coagulated by means of surgical instruments attached to surgical devices. If such tissue structures have nerves running through them, using such a surgical instrument can damage or destroy those nerves. If, for example, nerves in the face are damaged, the facial expressiveness of the patient can be impaired.

For this reason, it is common practice that when cutting or coagulating tissue that may has nerves running through it, a surgeon will apply a test current at the cutting or coagulation site to effect stimulation of the relevant muscle. From this test, it can be determined if a muscle region will be affected by the cut and a decision can then be made to make the cut elsewhere. However, to perform a test in this manner, a direct current or low-frequency alternating current must be available. This is usually provided via separate nerve testing equipment.

U.S. Patent Application Publication No. 2006/0184164 A1 discloses an HF surgery device with a surgical instrument that can be operated in cutting, coagulating, and stimulating modes. The device comprises a direct current supply which provides a test current for stimulating nerves, and an HF generator which provides high-frequency current for cutting or coagulating tissue. However, this HF surgical apparatus has a complex design and occupies a large amount of space.

WO 00/13600 discloses an HF surgical device with a high-frequency current instrument for treating motor nerves. As well as treating nerves, stimulation of nerves is possible and both functions can be carried out with the same device. The energy for treating the tissue is provided by an HF generator, whereas the energy for stimulating the tissue is provided by a pulse generator. However, the HF surgical instrument disclosed by WO 00/13600 is also relatively complex and bulky.

SUMMARY OF THE INVENTION

It is an object of the invention to disclose a surgical apparatus which can be produced with little effort and which is space-saving.

In particular, disclosed herein is a surgical device for testing nerves during an operation using an HF surgical generator and an electrosurgical instrument, the surgical device comprising a converter for converting a high-frequency treatment current from the HF surgical generator to a nerve-stimulating current, and a controllable selector switch on the device that controls which current is fed to the electrosurgical instrument.

An important point of the invention lies in the conversion of the high-frequency treatment current from the HF surgical generator so that the current can also be used for stimulating nerves. This eliminates the necessity for a separate direct current or low-frequency generator for nerve stimulation. Another benefit to using the converter is that the surgical apparatus is more compact than the devices known from the prior art, and also more easily manufactured. In this way costs can be saved.

The converter can comprise a rectifier circuit which generates a direct current (the nerve-stimulating current). Thus, in a particularly simple manner, the high-frequency treatment current of the HF surgical generator is converted into a suitable current for stimulating nerves.

In a further embodiment, the converter has a frequency divider for generating a low-frequency stimulating current, which also significantly uncomplicates converting the high-frequency treatment current of the HF surgical generator into a current suitable for stimulating the nerves.

The converter can also comprise a pulse modulation unit for creating a temporally defined pulse or pulse sequence of the nerve-stimulating current. This allows for the creation of suitable stimulation patterns.

In another embodiment, the converter comprises a constant current source for generating constant current strength for the nerve-stimulating current. This allows a surgeon to generate reproducible stimuli.

The constant current source is preferably adjustable to predetermined current strengths. This enables adaptation of the converter to the different tissues within the human body and to the different electrical resistance values thereof.

In yet another embodiment, the converter comprises a driver device that is connected to and controls output current parameters and voltage parameters of the HF surgical generator, which are adjustable to generate defined nerve stimulating current parameters. This is a simple option for adjusting defined nerve stimulating parameters.

The converter can arranged in a special housing or insert and configured to be connected to the surgical device via a plug connection or the like. An embodiment of this type is particularly suitable for equipping an existing surgical device with conversion capabilities.

BRIEF DESCRIPTION OF THE DRAWINGS

The invention will now be described, disclosing further features and advantages, using exemplary embodiments which are described in greater detail by reference to the figures, in which.

DETAILED DESCRIPTION OF THE INVENTIONS

In the following description, the same reference signs are used for the same and similarly acting parts.

Figure 1:
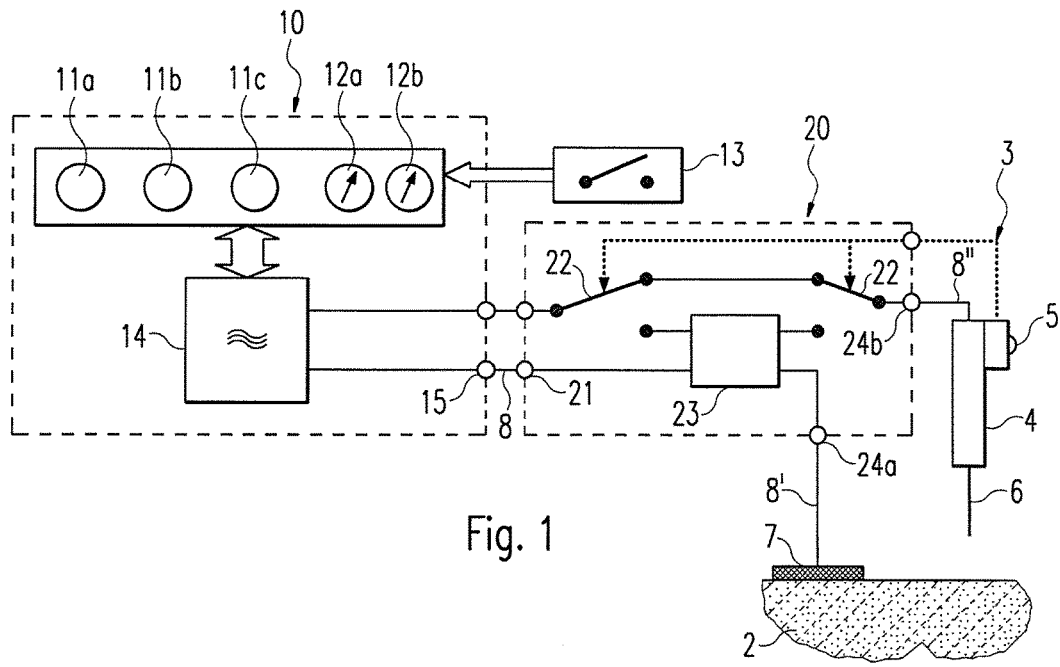
FIG. 1 shows a schematic representation of a surgical apparatus with an electrosurgical instrument attached and a section of tissue to be treated.

FIG. 1 shows a surgical device with a converter 20 and an HF surgical generator 10 and an attached electrosurgical instrument 4. A tissue section 2 to be treated or stimulated with the electrosurgical instrument 4 is also shown.

The HF surgical generator 10 comprises, in this case, an HF oscillator 14 as well as three operating elements 11a to 11c and two display elements 12a, 12b. Operation of the HF surgical generator 10 is controlled via a switch 13. The switch 13 is arranged outside the HF surgical generator 10 and connected thereto and be, for example, a foot switch. Switch 13 can also be wirelessly connected to HF surgical generator 10.

Various parameters such as frequency, voltage, current strength, etc., which characterize the output of HF generator 10 can be adjusted via operating elements 11a to 11c. Display elements 12a, 12b display these adjustable parameters and other parameters.

High-frequency treatment current from the HF generator is fed via connecting lines 8 to converter inputs 21 of the converter 20.

Depending on the setting of controllable selector switches 22, the high-frequency treatment current passes through the converter 20 either unchanged (this configuration is shown in FIG. 1) or, on account of its detour through a converter circuit 23, in converted form.

A first converter output 24a is connected via a connecting line 8' to a neutral electrode 7, which is connected to the tissue 2. A second converter output 24b is connected via a connecting line 8" to the electrosurgical instrument 4's active electrode 6.

The electrosurgical instrument 4 also comprises an operating element 5, which is connected via an information transmission unit 3 to control selector switches 22. This connection can be wired or wireless, for example, via infrared or radio connection. In the case of a wireless connection, the converter 20 and the electrosurgical instrument 4 will have corresponding (not shown in the drawings) receiving and transmitting devices to receive and transmit the relevant information.

Further information (apart from input/output control information) can also be exchanged via the information transmission units 3. For example, an error in the converter 20 can be shown on a display element (not shown in the drawings) of the electrosurgical instrument 4. Finer adjustment of the converter 20 can also be undertaken via the operating element 5 of the electrosurgical instrument 4 via displaceable or pivotable elements, for example, in relation to various parameters such as frequency, voltage, current, etc.

The converter 23 can comprise, for example, a rectifier circuit 25 (see FIG. 2) or a frequency divider (not shown in the drawings).

Figure 2:
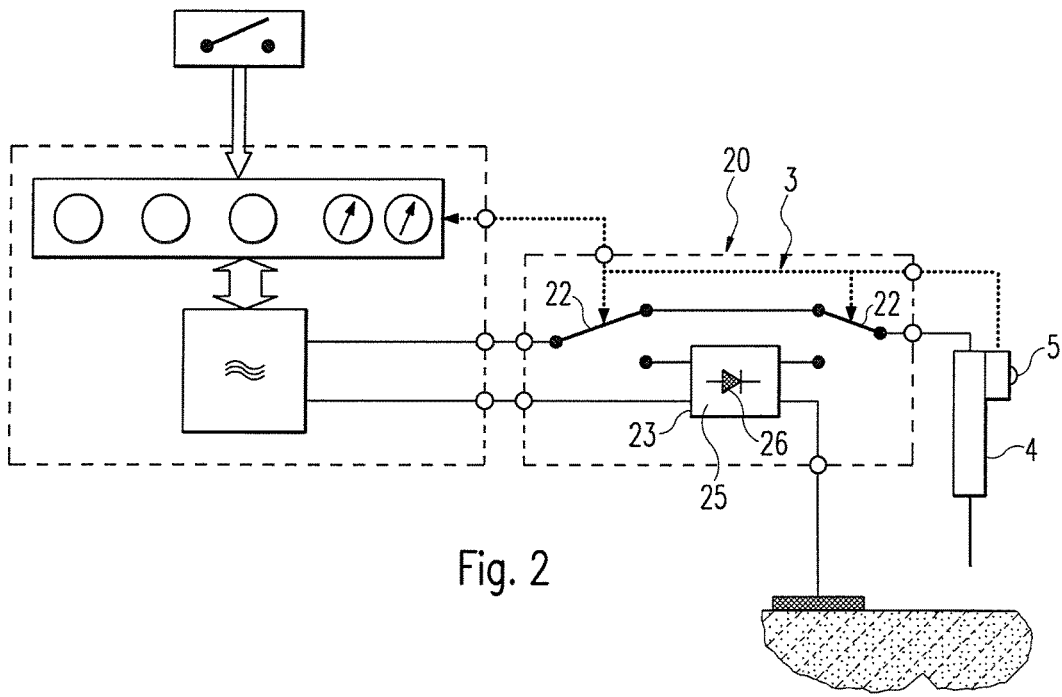
FIG. 2 shows another embodiment of a surgical apparatus with an electrosurgical instrument attached and the tissue to be treated as per FIG. 1.

In FIG. 2, the converter circuit 23 comprises a rectifier circuit 25 and diode 26. In the FIG. 2 embodiment, the operating element 5 of the electrosurgical instrument 4 is connected, via the information transmission unit 3, not only to the selector switches 22, but also to the HF surgical generator 10. Operating element 5, therefore, can control the output current parameters and the voltage parameters of the HF surgical generator 10 to adjust them to generate the desired nerve stimulating current.

As was shown in FIG. 1 and FIG. 2, the overall arrangement is essentially constructed from two modules, specifically the HF surgical generator 10 and the converter 20. Alternatively, it is also conceivable that the converter 20 could be integral component to the HF surgical generator 10. However, the modular design has the advantage that it is easier to retrofit commercially available HF surgical devices.

Figure 3:
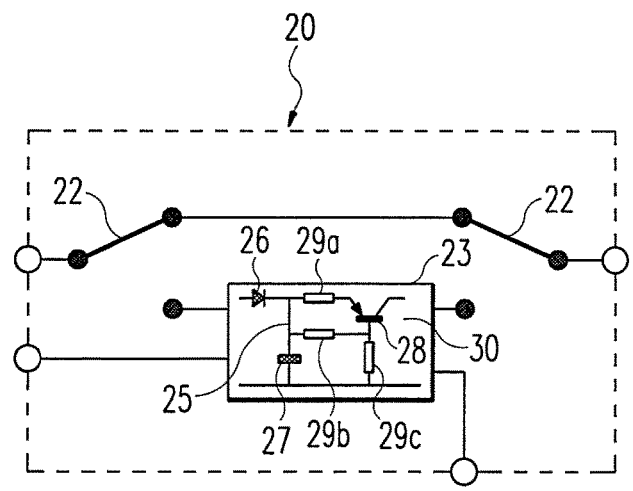
FIG. 3 shows another embodiment of the converter.

FIG. 3 shows an alternate embodiment of the converter circuit 23 of FIG. 2. The rectifier circuit 25 here consists of diode 26 and a capacitor 27, and a constant current source 30 is provided in known manner by a transistor 28 (in this case a pnp transistor) and resistors 29a to 29c.

Figure 4:
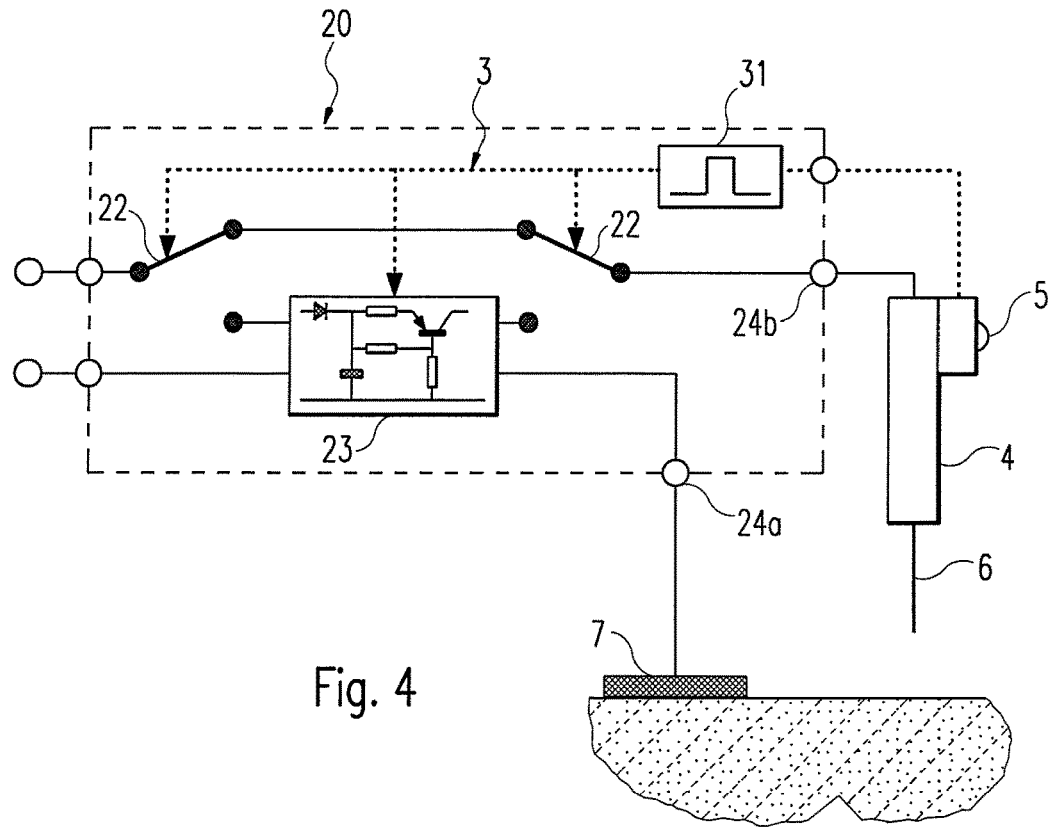
FIG. 4 shows the FIG. 3 converter in an electrosurgical instrument treating a tissue section as in FIGS. 1 and 2.

As FIG. 4 shows, the information transmission unit 3 can also connect operating element 5 of the electrosurgical instrument 4 to a converter circuit 23 (the FIG. 3 circuit is shown), so that adjustment of the converter 23 can be carried out via the operating element 5 of the electrosurgical element 4. Information and data from the converter circuit 23 can also be passed via the information transmission unit 3 to the electrosurgical instrument 4. In particular, it is possible to adjust the converter circuit 23 to have a predetermined current strength.

Also shown in FIG. 4, arranged between the electrosurgical instrument 4 and the converter circuit 23 is a pulse modulation unit 31 which is connected both to the converter circuit 23 and to the electrosurgical instrument 4 via the information transmission unit 3. The pulse modulation unit 31 serves to generate a temporally defined pulse or pulse sequences of the nerve stimulating current. Preferably, a single actuation of the operating element 5 leads to triggering of the pulse or pulse sequence such that the tissue is subjected to a stimulating current for only a desired (preferably short) time period and then cut or coagulated and renewed actuation of the operating element 5 for resetting cutting or coagulation operation is not necessary.

It should be noted at this point that all the parts described above are claimed as being essential to the invention both alone and in any combination, particularly the details shown in the drawings. Variations thereof belong to the common practice of a person skilled in the art.

REFERENCE SIGNS

2 Tissue section
3 Information transmission unit
4 Electrosurgical instrument
5 Operating element
6 Active electrode
7 Neutral electrode
8 Connecting line
10 HF surgical generator
11a, 11b, 11c Operating element
12a, 12b Display element
13 Switch
14 HF oscillator
20 Converter
21 Converter inputs
22 Selector switch
23 Converter circuit
24a, 24b Converter outputs
25 Rectifier circuit
26 Diode
27 Capacitor
28 Transistor
29a, 29b, 29c Resistor
30 Constant current source
31 Pulse modulation unit

The invention claimed is:

1. A surgical apparatus for facilitating testing nerves during high-frequency surgery, comprising:
   a high-frequency generator for generating a high-frequency treatment current,
   a converter for converting the high-frequency treatment current into a nerve stimulating current;
   connecting lines for feeding the high-frequency treatment current from the high-frequency generator to the converter; and
   a controllable selector switch for selectively feeding one of the high-frequency treatment current and the nerve stimulating current to a high-frequency electrosurgical instrument,
   wherein the converter comprises a rectifier circuit for generating a direct current as the nerve stimulating current.

2. The surgical apparatus of claim 1, wherein the converter comprises a pulse modulation unit for generating a temporally defined pulse or temporally defined pulse sequence of the nerve stimulating current.

3. The surgical apparatus of claim 1, wherein the converter comprises a constant current source for generating the nerve stimulating current, wherein the nerve stimulating current is constant.

4. The surgical apparatus of claim 3, wherein the constant current source is adjustable to predetermined current strengths.

5. The surgical apparatus of claim 1, wherein the converter comprises at least one driver device adapted to control output current parameters and voltage parameters of the high-frequency treatment current.

6. The surgical apparatus of claim 1, wherein the converter is arranged in a special housing or housing insert and configured such that said converter can be connected to the high-frequency electrosurgical instrument via a plug connection.

7. The surgical apparatus of claim 5, wherein the driver device is capable of adjusting the output current parameters and the voltage parameters of the high-frequency treatment current to match defined nerve stimulating current parameters.

* * * * *